(12) United States Patent
Van Herpen et al.

(10) Patent No.: US 8,039,814 B2
(45) Date of Patent: Oct. 18, 2011

(54) LUMINESCENCE SENSOR OPERATING IN REFLECTION MODE

(75) Inventors: Maarten Marinus Johannes Wilhelm Van Herpen, Eindhoven (NL); Derk Jan Wilfred Klunder, Eindhoven (NL); Hendrik Roelof Stapert, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/158,451

(22) PCT Filed: Dec. 19, 2006

(86) PCT No.: PCT/IB2006/054940
§ 371 (c)(1),
(2), (4) Date: Jun. 20, 2008

(87) PCT Pub. No.: WO2007/072415
PCT Pub. Date: Jun. 28, 2007

(65) Prior Publication Data
US 2008/0272313 A1 Nov. 6, 2008

(30) Foreign Application Priority Data
Dec. 22, 2005 (EP) .................................. 05112685

(51) Int. Cl.
*G01N 21/64* (2006.01)
(52) U.S. Cl. .................................................. 250/458.1
(58) Field of Classification Search ............... 422/82.08; 250/458.1
See application file for complete search history.

(56) References Cited

U.S. PATENT DOCUMENTS

| 2003/0132392 A1* | 7/2003 | Kuroda et al. ................ 250/397 |
| 2003/0174992 A1 | 9/2003 | Levene et al. |
| 2007/0154921 A1 | 7/2007 | Woudenberg |
| 2009/0305287 A1 | 12/2009 | Nordman |
| 2009/0305908 A1 | 12/2009 | Nordman |
| 2009/0305909 A1 | 12/2009 | Nordman |

FOREIGN PATENT DOCUMENTS

| EP | 0981051 A1 | 2/2000 |
| WO | 0214462 A1 | 2/2002 |
| WO | 03093807 A1 | 11/2003 |
| WO | 2006135782 A2 | 12/2006 |

(Continued)

OTHER PUBLICATIONS

A. G. Schuchinsky et al., "Enhanced transmission in microwave arrays of periodic sub-wavelength apertures," J. Opt. A: Pure Appl. Opt. 7 (2005) S102-S109. Published Jan. 20, 2005 by Institute of Physics Publishing. DOI:10.1088/1464-4258/7/2/014.*

(Continued)

*Primary Examiner* — Constantine Hannaher (57) ABSTRACT

A luminescence sensor, such as a luminescence biosensor or a luminescence chemical sensor, includes a substrate having at least one aperture filled with a medium. The aperture has a first lateral dimension larger than the diffraction limit of excitation radiation in the medium, and a second lateral dimension smaller than the diffraction limit of the excitation radiation in the medium. A method is also provided for the detection of luminescence radiation, e.g. fluorescence radiation, generated by at least one optically variable molecule, e.g. fluorophore, in the at least one aperture. Beneficially, the excitation radiation is polarized to suppress the excitation radiation in the apertures. The luminescence sensor and the method are able to detect relatively low concentrations of optically variable molecules, e.g. fluorophores.

20 Claims, 3 Drawing Sheets

FOREIGN PATENT DOCUMENTS

WO     2007070869 A2     6/2007

OTHER PUBLICATIONS

Q. Li et al., "Analysis of novel optical properties of subwavelength double-layers metallic grating," Appl. Phys. B 81 (2005) 787-790. Published Sep. 12, 2005 by Springer Verlag. DOI:10.1007/s00340-005-1945-8.*

D. W. Pohl, et al: Optical Stethoscopy: Image Recording with Resolution LAMBDA / 20, Applied Physics Letters, American Institute of Physics, vol. 44, No. 7, Apr. 1, 1984, pp. 651-653.

Martin Oheim, et al: Multiparameter Evanescent-Wave Imaging in Biological Fluorescence Microscopy, 2002 IEEE Journal of Quantum Electronics, IEEE Service Center, vol. 38, No. 2, Feb. 2002, pp. 142-148.

"Surface Plasmon Resonance" Wikipedia, Apr. 5, 2011, pp. 1-5.

Xu, M. et al "Wire-Grid Diffraction Gratings used as Polarizing Beam Splitter for Visible Light and Applied in Liquid Crystal on Silicon", Optics Express, vol. 13, No. 7, Apr. 4, 2005.

Yeh, Pochi, "A New Optical Model for Wire Grid Polarizers" Optics Communications, vol. 26, No. 3, Sep. 1978, pp. 289-292.

Kim, Doughyun et al "Design and Development of Grating Coupled Optical Biosensor to Detect Animal Pathogen", Biomedical Vibrational Spectroscopy/Biohazard Detection Technologies, Proc. of SPIE, vol. 5321, pp. 309-314.

Weiner, J., "The Physics of Light Transmission through Subwavelength Apertures and Aperture Arrays", Reports on Progress in Physics, vol. 72, 2009, pp. 1-19.

* cited by examiner

LUMINESCENCE SENSOR OPERATING IN REFLECTION MODE

The present invention relates to qualitative and/or quantitative luminescence sensors, such as luminescence biosensors or luminescence chemical sensors, working in reflection mode. More particularly, the invention relates to luminescence sensors comprising at least one aperture filled with a medium. The invention furthermore relates to a method for the detection of luminescence radiation generated by one or more luminophores present in an aperture or slit structure in such a luminescence sensor.

Sensors are widely used for measuring a physical attribute or a physical event. They output a functional reading of that measurement as an electrical, optical or digital signal. That signal is data that can be transformed by other devices into information. A particular example of a sensor is a biosensor. Biosensors are devices that detect the presence of (i.e. qualitative) or measure a certain amount (i.e. quantitative) of target molecules such as e.g., but not limited thereto, proteins, viruses, bacteria, cell components, cell membranes, spores, DNA, RNA, etc. in a fluid, such as for example blood, serum, plasma, saliva, . . . The target molecules are also called the "analyte". In almost all cases, a biosensor uses a surface that comprises specific recognition elements for capturing the analyte. Therefore, the surface of the sensor device may be formed from a specific binding material or may be modified by attaching specific molecules to it, which are suitable to bind the target molecules which are present in the fluid.

For optimal binding efficiency of the analyte to the specific molecules, large surface areas and short diffusion lengths are highly favourable. Therefore, micro- or nano-porous substrates (membranes) have been proposed as biosensor substrates that combine a large area with rapid binding kinetics. Especially when the analyte concentration is low (e.g. below 1 nM, or below 1 pM) the diffusion kinetics play an important role in the total performance of a biosensor assay.

The amount of bound analyte may be detected by luminescence, e.g. fluorescence. In this case the analyte itself may carry a luminescent, e.g. fluorescent, label, or alternatively an additional incubation with a luminescently labelled, e.g. fluorescently labelled second recognition element may be performed.

Detecting the amount of bound analyte can be hampered by several factors, such as scattering, bleaching of the luminophore, background luminescence of the substrate and incomplete removal of excitation light. Moreover, to be able to distinguish between bound labels and labels in solution it is necessary to perform one or more washing step to remove unbound labels.

In luminescence sensors with sub-diffraction-limited spatial resolution operating inside a fluid, light is reflecting on sub-diffraction-limited apertures or slits. This yields an evanescent field within the apertures or slits, which may be used for exciting luminophores present there. The luminescence sensor is irradiated with excitation radiation from a first side of the sensor. Luminescence that is generated may exit the apertures or slits of the sensor at the side opposite to the first side, i.e. opposite to the side at which the sensor is irradiated, and may be detected there, in that way separating excitation and luminescence radiation. Alternatively, luminescence generated by luminophores may exit the apertures or slits at the first side, i.e. at the same side at which the sensor is irradiated and may then be detected there.

US 2003/0174992 A1 describes how sub-diffraction limited apertures are used in a biosensor. The apertures have their lateral dimensions below the diffraction limit of the excitation light, which means that the excitation light is unable to travel through these apertures. This yields an evanescent field within the apertures. Fluorescence radiation is detected at the same side at which the sensor is irradiated. However, the combination of the penetration depth of this evanescent field with the lateral dimensions of the apertures leads to a very small excitation volume. The chance that a fluorophore enters an aperture is low in view of the limited lateral dimensions thereof. As a result, there is typically at most one fluorophore inside the excitation volume, even with relatively high concentrations of fluorophores outside the aperture. The limitations on the number of fluorophores in the aperture make it difficult to measure relatively low concentrations of fluorophores.

It is an object of the present invention to provide improved qualitative or quantitative luminescence sensors, such as e.g. luminescence biosensors or luminescence chemical sensors, comprising apertures or slit structures, and a method for the detection of luminescence radiation generated by one or more optically variable molecules, e.g. luminophores, present in at least one aperture or slit structure in such a luminescence sensor. An advantage of the present invention is being able to measure relatively low concentrations of optically variable molecules, such as luminophores.

More particularly, the invention relates to luminescence sensors comprising at least one aperture having a first lateral dimension larger than the diffraction limit of the excitation radiation in a medium the at least one aperture is filled with. The apertures also have a second lateral dimension below the diffraction limit of the excitation radiation in the medium the at least one aperture is filled with.

Particular and preferred aspects of the invention are set out in the accompanying independent and dependent claims. Features from the dependent claims may be combined with features of the independent claims and with features of other dependent claims as appropriate and not merely as explicitly set out in the claims.

In a first aspect of the invention, a luminescence sensor, such as e.g. a luminescence biosensor or luminescence chemical sensor, is provided. The luminescence sensor comprises:
  at least one aperture, being for being filled with a medium,
  at least one optically variable molecule present in the at least one aperture,
  an excitation radiation source for irradiating the at least one aperture with excitation radiation for exciting the at least one optically variable molecule, and
  a detector for detecting luminescence radiation generated by the at least one optically variable molecule,
wherein the at least one aperture has a first lateral dimension larger than the diffraction limit of the excitation radiation in the medium and a second lateral dimension lower than the diffraction limit of the excitation radiation in the medium and wherein the excitation radiation source and the detector are positioned at a same side of the sensor.

According to embodiments of the invention the at least one aperture may, for example, be a slit or an ellipsoid apertures or may be any other aperture with a first lateral dimension larger than the diffraction limit of the excitation radiation in the medium the at least one aperture is filled with and a second lateral dimension below the diffraction limit of the excitation radiation in the medium the at least one aperture is filled with.

The optically variable molecules may be molecules with which analyte molecules are labelled, and which always luminesce upon being irradiated by an illumination beam. Bound optically variable molecules are visualised, while non-bound optically variable molecules are washed away. Alternatively, the optically variable molecules may be marker molecules with which the analyte molecules are labelled, and which only luminesce when they are bound to molecules attached o a substrate. This makes a donor-acceptor pair. Washing is used to obtain stringency. Lightly bound molecules are washed away. In still another embodiment, molecules attached to a substrate luminesce when an analyte molecule binds to them. Washing is used to obtain stringency. Lightly bound molecules are washed away.

Alternatively, an analyte molecule to be detected can, upon irradiation with excitation radiation, e.g. excitation light, luminesce, e.g. fluoresce, itself. In that case, no labels are required and the analyte molecule itself acts as the optically variable molecule.

The detector may, for example, be a CCD or a CMOS detector. According to an embodiment of the invention, the luminescence sensor may be a luminescence biosensor such as e.g. a fluorescence biosensor.

According to the invention, the excitation radiation source and the detector for detecting luminescence, e.g. fluorescence, radiation are positioned at a same side of the sensor. This means that the sensor according to the invention operates in reflection mode. An advantage of a sensor operating in reflection mode with respect to a sensor operating in transmission mode is that more luminescence radiation, e.g. fluorescence radiation, can be collected. Moreover, by using apertures having dimensions as described above, the sensor according to the present invention can be used for the detection of relatively low concentrations of luminophores.

Hence, the luminescence sensor according to the present invention has a substantially higher efficiency, i.e. ratio between the power of the detected luminescence, e.g. fluorescence, radiation and the power of the excitation radiation, e.g. light, for an optically variable molecule, for example a luminophore, e.g. fluorophore, present in the aperture, than the prior art biosensors.

According to embodiments of the invention, the second lateral dimension of the apertures may be smaller than 50% of the wavelength of the excitation radiation, e.g. light, in the medium the at least one aperture is filled with. More preferably, the second lateral dimension of the apertures may be smaller than 40% of the wavelength of the excitation radiation, e.g. light, in the medium the at least one aperture is filled with. The latter corresponds with 80% of the diffraction limit of the excitation radiation, e.g. light, in the medium the at least one aperture is filled with and thus, preferably the second lateral dimension of the apertures may be smaller than 80% of the diffraction limit of the excitation radiation, e.g. light, in the medium the at least one aperture is filled with.

According to embodiments of the invention, the excitation radiation, e.g. light, may have a wavelength and the first lateral dimension may be larger than the diffraction limit of the excitation radiation, e.g. light, in the medium the apertures are filled with, but may at the same time be below the wavelength of the excitation radiation, e.g. light.

In embodiments of the invention, the first lateral dimension may be larger than the wavelength of the radiation emitted from the optically variable molecules, i.e. larger than the wavelength of the luminescence, e.g. fluorescence, radiation.

According to embodiments of the invention, the apertures comprise inner surface walls and ligands may be immobilised on the inner surface walls of the apertures. By using immobilised ligands that recognise one or more targets of interest, the selectivity of the luminescence sensor, for example luminescence biosensor or luminescence chemical sensor, may be improved.

Preferably, the excitation radiation, e.g. light, may be polarised to suppress the excitation radiation behind and in some cases also inside the apertures. Preferably, behind the optically variable molecule, i.e. at that side of the optically variable molecule opposite to the side of the optically variable molecule at which the excitation radiation source is positioned, the excitation radiation, e.g. excitation light, is suppressed as much as possible. On the other hand, the excitation radiation in front of the optically variable molecule, i.e. at that side of the optically variable molecule at which the excitation radiation source is positioned, may preferably be as high as possible, i.e. may preferably not be suppressed.

The luminescence sensor according to embodiments of the invention may comprise an array of apertures. The array of apertures may, in some embodiments, be a periodic array of apertures.

According to embodiments of the invention, the luminescence sensor may furthermore comprise a wavelength filter in between the sensor and the detector for suppression of reflected excitation radiation. The aim of this filter is thus to block unwanted excitation radiation that is reflected by the apertures. The wavelength filter should show a strong suppression, preferably better than two orders of magnitude, for the excitation radiation, e.g. light, but should show substantially no suppression for the luminescence, e.g. fluorescence, radiation. The transmission of luminescence, e.g. fluorescence, radiation, may preferably be better than 10% and more preferably may be better than 50%.

In a second aspect of the invention a method is provided for detecting luminescence radiation generated by at least one optically variable molecule present in at least one aperture of a sensor, the at least one aperture being for being filled with a medium. The method comprises:

exciting the at least one optically variable molecule by means of excitation radiation emanating from an excitation radiation source positioned at a front side of the at least one aperture, detecting luminescence radiation generated by the excited at least one optically variable molecule, wherein the at least one aperture has a first lateral dimension larger than the diffraction limit of the excitation radiation in the medium the apertures are filled with and a second lateral dimension below the diffraction limit of the excitation radiation in the medium the apertures are filled with. The method furthermore includes detecting the luminescence radiation on the same side of the sensor as where the excitation radiation source is positioned.

According to embodiments of the invention the at least one aperture may, for example, be a slit or an ellipsoid aperture or may be any other aperture with a first lateral dimension larger than the diffraction limit of the excitation radiation in the medium the at least one aperture is filled with and a second lateral dimension below the diffraction limit of the excitation radiation in the medium the at least one aperture is filled with.

The optically variable molecules may be molecules with which analyte molecules are labelled, and which always luminesce upon being irradiated by an illumination beam. Bound optically variable molecules are visualised, while non-bound optically variable molecules are washed away. Alternatively, the optically variable molecules may be marker molecules with which the analyte molecules are labelled, and which only luminesce when they are bound to molecules attached o a substrate. This makes a donor-acceptor pair. Washing is used to obtain stringency. Lightly bound molecules are washed away. In still another embodiment, molecules attached to a substrate luminesce when an analyte molecule binds to them. Washing is used to obtain stringency. Lightly bound molecules are washed away.

Alternatively, an analyte molecule to be detected can, upon irradiation with excitation radiation, e.g. excitation light, luminesce, e.g. fluoresce, itself. In that case, no labels are required and the analyte molecule itself acts as the optically variable molecule.

The detector may, for example, be a CCD or a CMOS detector. According to an embodiment of the invention, the luminescence sensor may be a luminescence biosensor such as e.g. a fluorescence biosensor.

According to the invention, exciting the optically variable molecules and detecting luminescence, e.g. fluorescence, radiation are both performed at a same side of the sensor. This means that the method according to the invention is performed in reflection mode. An advantage of detecting optically variable molecules or luminophores in reflection mode with respect to detecting them in transmission mode is that more luminescence radiation, e.g. fluorescence radiation, can be collected, i.e. that the efficiency of the measurement is higher. Moreover, by using a sensor comprising apertures having dimensions as described above, the method according to the present invention can be used for the detection of relatively low concentrations of luminophores.

Hence, the method according to the present invention has a substantially higher efficiency, i.e. ratio between the power of the detected luminescence, e.g. fluorescence, radiation and the power of the excitation radiation, e.g. light, for a luminophore, e.g. fluorophore, present in the aperture, than the prior art methods for detecting optically variable molecules.

According to embodiments of the invention, the second lateral dimension of the apertures may be smaller than 50% of the wavelength of the excitation radiation, e.g. light, in the medium the at least one aperture is filled with. More preferably, the second lateral dimension of the apertures may be smaller than 40% of the wavelength of the excitation radiation, e.g. light, in the medium the at least one aperture is filled with. The latter corresponds with 80% of the diffraction limit of the excitation radiation, e.g. light, in the medium the at least one aperture is filled with and thus, preferably the second lateral dimension of the apertures may be smaller than 80% of the diffraction limit of the excitation radiation, e.g. light, in the medium the at least one aperture is filled with.

According to embodiments of the invention, the excitation radiation, e.g. light, may have a wavelength and the first lateral dimension may be larger than the diffraction limit of the excitation radiation, e.g. light, in the medium the apertures are filled with, but may at the same time be below the wavelength of the excitation radiation, e.g. light.

Preferably, the method according to the present invention may be performed by using excitation radiation, e.g. light, that consists of TE polarised radiation, e.g. TE polarised light, with TE polarised radiation, e.g. light, defined as radiation, e.g. light, with its electric field directed along the first lateral dimension of the aperture(s).

According to embodiments of the invention, the apertures comprise inner surface walls and the method may furthermore comprise immobilising ligands on the inner surface walls of the apertures. By immobilising ligands that recognise one or more targets of interest on the inner surface walls of the apertures the selectivity of the luminescence sensor, for example luminescence biosensor or luminescence chemical sensor, used to perform the method according to the present invention may be improved.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

In the different figures, the same reference signs refer to the same or analogous elements.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The present invention provides a luminescence sensor, such as, for example, a luminescence biosensor or a luminescence chemical sensor. Hereinafter, the present invention will mainly be described with reference to a luminescence biosensor, but this is only for the ease of explanation and does not limit the invention.

The luminescence sensor according to the present invention comprises a substrate provided with at least one aperture. According to embodiments of the invention, the sensor may comprise an array of apertures. The array of apertures may, in some embodiments, be a periodic array of apertures. In use the at least one aperture is filled with a medium. The medium may be a liquid or a gas, but may also be vacuum. In some embodiments the medium includes at least one optically variable molecule, for example a luminescent particle, e.g. fluorescent particle, to be detected. These particles to be detected will be described as "optically variable molecules" or "luminophores". Such molecules can be, for instance, fluorescent, electroluminescent, chemoluminescent molecules, etc. The optically variable molecule may be used for labelling an analyte present in the medium.

There are at least three possible situations for using optically variable molecules in the labelling of an analyte:
1) Analyte molecules are labelled with optically variable molecules which always luminesce, e.g. fluoresce. Those molecules which are bound can be visualised, all other optically variable molecules can be washed away.
2) Analyte molecules are labelled with marker molecules which only luminesce, e.g. fluoresce, when they are bound to molecules attached to a substrate. In that way a donor acceptor pair is formed. A washing step is in this case used to obtain stringency as lightly bound molecules will be washed away.
3) Molecules attached to a substrate luminesce, e.g. fluoresce, when an analyte molecule binds to them. Washing is again used to obtain stringency as lightly bound molecules are washed away.

Alternatively, an analyte molecule to be detected can, upon irradiation with excitation radiation, e.g. excitation light, luminesce, e.g. fluoresce, itself. In that case, no labels are required and the analyte molecule itself acts as the optically variable molecule.

The present invention will be described for optically variable molecules, i.e. luminescent labels, being attached to an analyte in the medium, the analyte binding to recognition labels being washed away, the labels luminescing when being irradiated by an illumination beam scanning the sensor and impinging onto them. It has to be understood that this is not limiting the invention and that the invention also applies in the other cases described above.

The sensor is for use with a source of excitation radiation, e.g. a light source. The light source emits light at a certain wavelength or range of wavelengths. . A sensor with similar excitation characteristics for other wavelengths can be obtained by scaling the dimensions of the at least one aperture with the wavelength of the excitation radiation, e.g. excitation light, provided that the wavelength dependence of the refractive indexes of the aperture materials and the materials that fills the at least one aperture is reasonably moderate. For example, in case where the generated luminescence radiation is fluorescence radiation, the optical wavelength (in vacuum) of the excitation radiation typically may range from 300 to 2000 nm and preferably may be in the range from 400 to 1100 nm.

According to the invention, at least one luminophore, e.g. fluorophore, is present in the at least one aperture for being excited by an excitation radiation, for example excitation light, having a particular wavelength. The at least one aperture has a first lateral dimension larger than the diffraction limit of the excitation radiation, e.g. excitation light, in the medium the at least one aperture is filled with and a second lateral dimension below the diffraction limit of the excitation radiation, e.g. excitation light, in the medium the at least one aperture is filled with. Preferably, the second lateral dimension may be smaller than 80% of the diffraction limit of the excitation radiation in the medium the apertures are filled with (see further). With lateral dimensions are meant the dimensions of the aperture in the plane of the surface of the substrate, i.e. the lateral dimensions do not include the depth in the substrate. The term "aperture" should be interpreted widely. For example, apertures which may be applied with the sensor of the present invention could be slits, holes, gaps or ellipsoid apertures, but the invention is not limited thereto.

It is known that almost no radiation, e.g. light, is being transmitted by the apertures when the lateral dimensions of the apertures are smaller than half the wavelength of the incident radiation in the medium the at least one aperture is filled with. In general, in order for the radiation not to propagate inside the at least one aperture, evanescent waves are required, which are waves with spatial frequencies beyond the diffraction limit. This means that for a given wavelength $\lambda$, a given refractive index n of the medium that fills the apertures, i.e. e.g. the medium in which the sensor is immersed, and a properly chosen polarisation (see further), the smallest lateral dimension of the apertures should be smaller than $\lambda/(2*n)$. Thus, only evanescent fields are able to penetrate into the apertures if use is made of apertures with one lateral dimension, e.g. a width, smaller than the diffraction limit in an immersion fluid, e.g. smaller than 270 nm for water (at an excitation wavelength of 700 nm) if the structure is immersed in water.

Hereinafter, the invention will be described by means of apertures having lateral dimensions defined with respect to the diffraction limit of the medium the apertures are filled with.

The present invention will furthermore be described with respect to a luminescence sensor device for being immersed in a medium, e.g. a fluid. However, this is not limiting the invention. The luminescence sensor device according to the present invention comprises at least one aperture for being filled with the medium, the at least one aperture having a first lateral dimension larger than the diffraction limit of the excitation radiation in the medium and a second lateral dimension below the diffraction limit of the excitation radiation in the medium. The luminescence sensor does not need to be immersed in the medium; the medium may also e.g. be sprayed over the sensor and into the at least one aperture having one lateral dimension larger than the diffraction limit of the excitation radiation in the medium and one lateral dimension below the diffraction limit of the excitation radiation in the medium, preferably below the diffraction limit of the medium, e.g. fluid, these apertures are filled with.

The present invention provides a luminescence sensor, such as, for example, a luminescence biosensor or a luminescence chemical sensor, using apertures having lateral dimensions as described above and being operated in 'reflection mode'. An advantage hereof is that the luminescence sensor according to the present invention will have an extra efficiency, i.e. the ratio between the power of the detected luminescence, e.g. fluorescence, radiation and the power of the excitation radiation compared to luminescence sensors which are operated in 'transmission mode'.

Hereinafter, the difference between 'transmission mode' and 'reflection mode' will be explained. The explanation will be made for a sensor comprising slits having a first lateral dimension or length L with a dimension larger than the diffraction limit of the excitation radiation in the medium the apertures are filled with and a second lateral dimension or width w lower than the diffraction limit of the excitation radiation in the medium the apertures are filled with. It has, however, to be understood, that this also applies to sensors comprising any other aperture than slits, as long as these apertures have a first lateral dimension larger than the diffraction limit of the excitation radiation in the medium and a second lateral dimension below the diffraction limit of the excitation radiation in the medium, such as, for example, an ellipsoid aperture.

Figure 1:
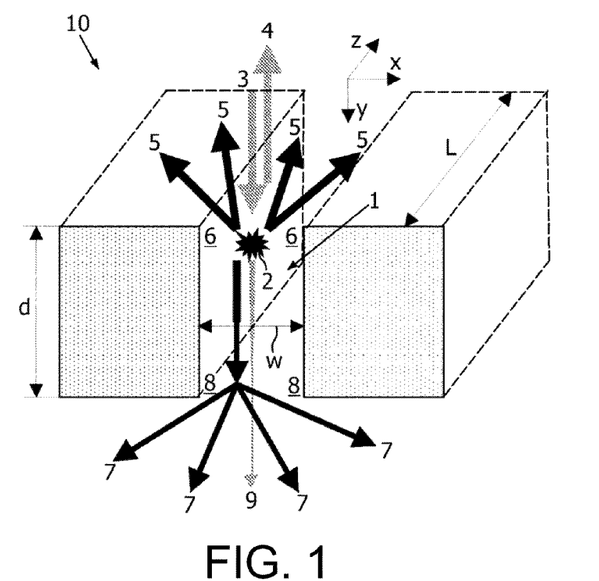
FIG. 1 is a schematic illustration of 'transmission mode' and 'reflection mode' in a luminescence sensor with a slit aperture.

FIG. 1 is a schematic illustration of such a luminescence sensor 10, wherein a slit 1 is used for evanescent excitation of luminophores 2, e.g. fluorophores. This may be achieved by illuminating the slit 1 with e.g. TE polarized (E field along the long-direction of the slits 1) excitation radiation 3, e.g. excitation light, that is reflected by the slits 1, because the diffraction limit of the excitation radiation 3, e.g. excitation light, in the medium that fills the slits 1 is larger than the width w of the slit 1. This yields a reflected beam 4.

Within the slit 1 an evanescent field is present that is used to excite the luminophores 2, e.g. fluorophores, yielding luminescence radiation, e.g. fluorescence radiation, that is emitted in all directions. Luminescence radiation 5, e.g. fluorescence radiation, is emitted in the direction of a front side 6 of the slit 1, i.e. that side which is irradiated, and luminescence radiation 7, e.g. fluorescence radiation, is emitted towards a back side 8 of the slit 1, i.e. that side which is located opposite to the side which is irradiated. Most of the excitation radiation 3, e.g. excitation light, is reflected into reflected beam 4, but some excitation radiation, e.g. excitation light, which is in FIG. 1 indicated by reference number 9, may leak out of the sensor 10 at the back side 8 of the slit 1. However, this remaining excitation radiation 9, e.g. excitation light, is substantially suppressed by the slit 1 and therefore it is of low intensity.

Throughout the further description of the present invention reference will be made to 'transmission mode' and 'reflection mode'. The difference between these modes is that in 'reflection mode' luminescence radiation 5, e.g. fluorescence radiation, which is propagating substantially contra-directional to the direction of the excitation radiation 3, e.g. excitation light, is collected at a detector which is positioned at the front side 6 of the slit 1 or at a same side of the slit 1 at which an excitation radiation source (not shown in FIG. 1) is positioned for irradiating the sensor 10, whereas in 'transmission mode' luminescence radiation 7, e.g. fluorescence radiation, which is propagating in substantially the same direction as the excitation radiation 3, e.g. excitation light, is detected at a detector positioned at the back side 8 of the slit 1 or at the opposite side than the side where the excitation radiation source is positioned.

As can be seen in FIG. 1, the advantage of using a luminescence sensor in 'transmission mode' is that the ratio between the collected luminescence radiation 7 (assuming that all excitation radiation 3 directed away from the back/front side for a sensor operated in 'transmission'/'reflection' mode respectively is detected by the detector 12) and collected excitation radiation is larger than in 'reflection mode'. This is because the excitation radiation 9, e.g. excitation light, is being suppressed as it travels through the slit 1. The slit 1 suppresses luminescence radiation 7, e.g. fluorescence radiation, much less, because in most cases the orientation of the luminophores 2, e.g. fluorophores, is random, i.e. including TE and TM luminescence radiation, and the slit 1 suppresses TE polarised radiation (direction of electric field in the long dimension of the slit 1), e.g. TE polarised light, stronger than TM polarised radiation (direction of electric field in the small dimension of the slit 1), e.g. TM polarized light. However, still a substantial part, i.e. about 50%, of the luminescence radiation 7, e.g. fluorescence radiation, is being suppressed by the slit 1. Therefore, the advantage of using 'reflection mode' with respect to using 'transmission mode' is that more luminescence radiation 5, e.g. fluorescence radiation, can be collected.

'Reflection mode' as introduced by the present invention in apertures having a first lateral dimension larger than the diffraction limit of the excitation radiation and a second lateral dimension lower than the diffraction limit of the excitation radiation is not compatible with current prior art sensors because:

the reflection mode system as described above in US 2003/0174992 A1 is less suitable for detecting relatively low concentrations of luminophores, e.g. fluorophores, due to the low chance of a molecule travelling into an aperture having all lateral dimensions smaller than the diffraction limit of the excitation radiation in the medium the apertures 1, e.g slits, are filled with, Biosensor based on 2D sub-diffraction-limit apertures, i.e. apertures 1 having sub-diffraction limit dimensions in both lateral directions, have a significantly worse transmission of luminescent, e.g. fluorescent, radiation 5 than the sensor 10 according to the present invention. This is because the luminescence, e.g. fluorescence, radiation 5 generated inside the aperture 1 can only couple to evanescent fields that are substantially suppressed.

Therefore, the present invention provides a luminescence sensor 10 that works in 'reflection mode' and has a substantially higher efficiency, i.e. ratio between the power of the detected luminescence, e.g. fluorescence, radiation and the power of the excitation radiation, e.g. light, for a luminophore, e.g. fluorophore, present in the aperture, than the biosensor described in US 2003/0174992.

Figure 2:
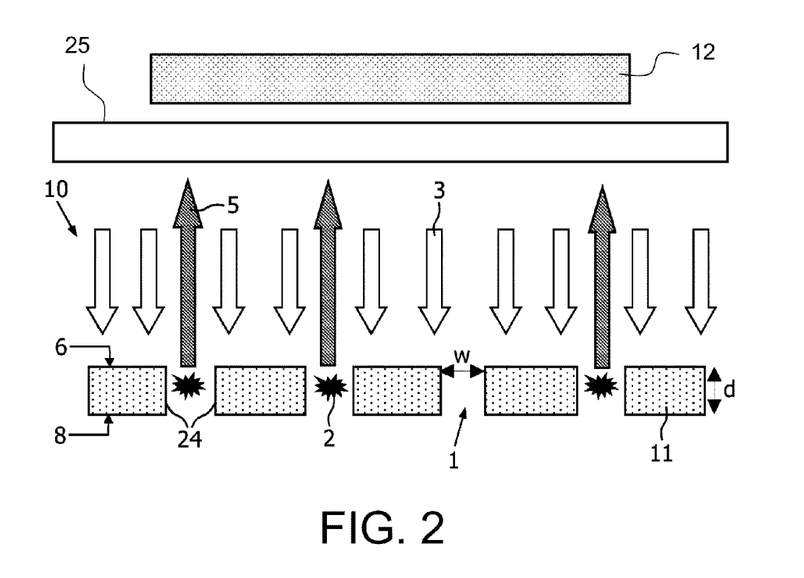
FIG. 2 is a schematic illustration of a sensor according to an embodiment of the present invention.

In a first embodiment of the present invention, a luminescence sensor 10 such as, for example, a luminescence biosensor or luminescence chemical sensor is provided (see FIG. 2). The luminescence sensor 10 comprises a substrate 11 provided with at least one aperture 1 having a first lateral dimension larger than the diffraction limit of the excitation radiation in a medium the at least one aperture 1 is filled with and a second lateral dimension w below the diffraction limit of the excitation radiation in the medium. According to embodiments of the invention, the first lateral dimension may be larger than the diffraction limit of the excitation radiation 3, e.g. excitation light, in the medium the apertures 1 are filled with, but may at the same time be lower than the wavelength of the excitation radiation 3, e.g. excitation light. Preferably, the second lateral dimension w of the at least one aperture 1 may be smaller than 50% of the wavelength of the excitation radiation 3 in the medium with which the at least one aperture 1 is filled, most preferably smaller than 40% of the wavelength of the excitation radiation 3 in the medium with which the at least one aperture 1 is filled. The latter corresponds with 80% of the diffraction limit of the excitation radiation 3 in the medium the at least one aperture 1 is filled with.

The first and second lateral dimensions may be length L and width w of the apertures 1. The aperture 1 as defined above can have a certain elongate form as there is a difference in dimensions in two directions. Examples of apertures 1 which can be used with the present invention are slits or ellipsoid apertures.

In embodiments of the present invention, the term "substrate" may include any underlying material or materials that may be used, or upon which a device, a circuit or an epitaxial layer may be formed, provided that at least part of it is not transparent for the excitation light. In other alternative embodiments, this "substrate" may include a semiconductor substrate such as e.g. a doped silicon, a gallium arsenide (GaAs), a gallium arsenide phosphide (GaAsP), an indium phosphide (InP), a germanium (Ge), or a silicon germanium (SiGe) substrate. The "substrate" may include for example, an insulating layer such as a $SiO_2$ or an $Si_3N_4$ layer in addition to a semiconductor substrate portion. Thus, the term substrate also includes silicon-on-glass, silicon-on sapphire substrates. The term "substrate" is thus used to define generally the elements for layers that underlie a layer or portions of interest. Also, the "substrate" may be any other base on which a layer is formed, for example a glass, plastic or metal layer. For example, at least one aperture 1 may be formed in a non-transparent material which is deposited on top of a glass plate or another transparent substrate. In another example, at least one aperture 1 may be defined and etched through a layer that is non-transparent for the excitation radiation 3, e.g. excitation light, without having a support underneath such that e.g. fluids can flow through the substrate 11.

The main requirement for the substrate material is that, next to the apertures 1, it is not transparent for the excitation radiation 3, e.g. excitation light, in other words, that the substrate material has a large attenuation for the excitation radiation 3. This implies that at least part of the material stack where the apertures 1 extend into should be non-transparent for the excitation radiation 3, e.g. excitation light, or that the substrate material between the apertures 1 is not transparent for the excitation radiation 3, e.g. excitation light. This is important, even in the case of the present invention, where the measurements are performed in reflection because in case the material stack is completely transparent while still having apertures 1 with a least one lateral dimension below the diffraction limit of the excitation radiation 3, e.g. light, the excitation radiation 3, e.g. light, can propagate through the layer stack.

According to embodiments of the invention the wafer substrate 11 may comprise an array of apertures 1 with lateral dimensions as described above. The array of apertures 1 may, according to embodiments of the invention, be a periodic array of apertures 1, i.e. an array having an equal distance between neighbouring apertures 1. However, this does not need to be so; the distance between neighbouring apertures 1 may also be different or variable.

When using apertures 1 having a first lateral dimension larger than the diffraction limit of the excitation radiation, e.g. light, in a medium the apertures 1 are filled with, and a second lateral dimension below the diffraction limit, of the excitation radiation, e.g. light, in a medium the apertures 1 are filled with, a better detection efficiency can be obtained compared to using sub-wavelength pin-holes with all lateral dimensions being lower than the diffraction limit of the medium the pin-holes are filled with. This is because suppression of the luminescence radiation, e.g. fluorescence radiation, is much less in the first case, as this suppression is polarization dependent. This polarisation dependence will be explained hereinafter by means of a sensor comprising at least one slit 1. It has, however, to be understood that this is not limiting to the invention and that this may be applied to sensors comprising any apertures 1 having a first lateral dimension larger than the diffraction limit of the excitation radiation in a medium the apertures 1 are filled with and a second lateral dimension below the diffraction limit, preferably 80% or less of the diffraction limit of the excitation radiation 3, e.g. excitation light, in a medium the apertures 1 are filled with.

Figure 3:
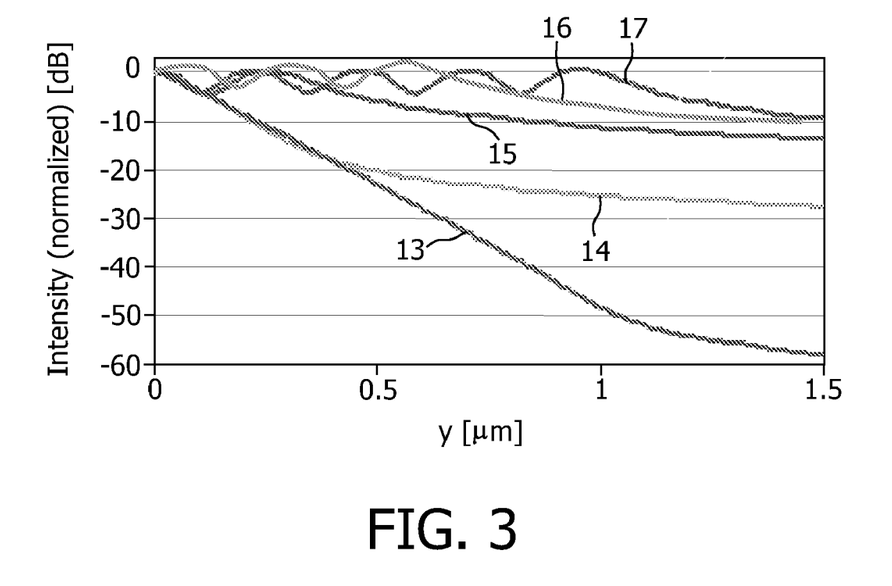
FIG. 3 shows the normalised intensity (normalised with respect to intensity at x=y=0) along the centre line of a slit for TE and TM polarisation and for different widths (w) of slits.
Figure 4:
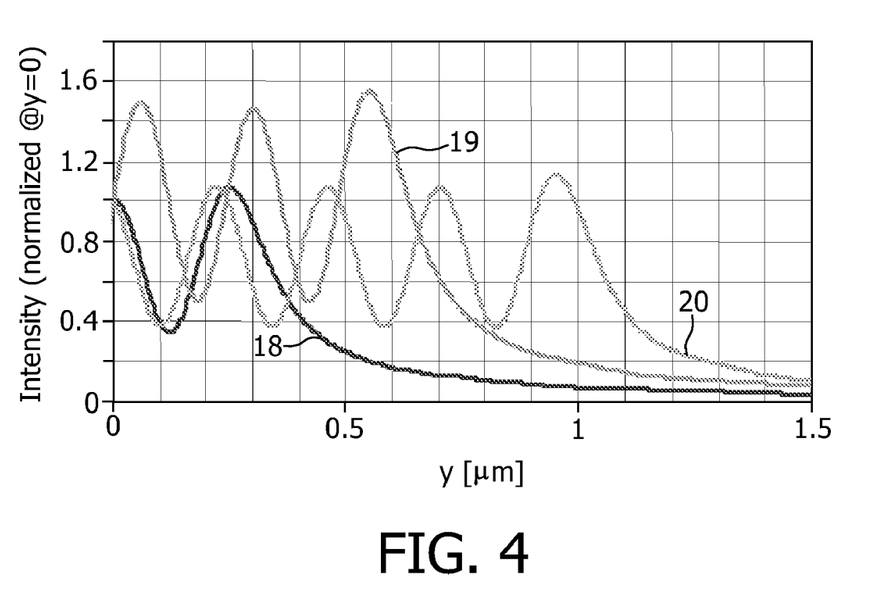
FIG. 4 shows the normalised intensity (normalised with respect to intensity at x=y=0) along the centre line of a slit for TM polarisation.

Hereinafter, an explanation will be given on how the field decays inside the apertures 1 and why TM polarized luminescence radiation can escape from the aperture 1. FIGS. 3 and 4 show the normalised intensity (normalised with respect to intensity at x=y=0) along the centre (x=0) of a slit 1. In the calculations a slit in a gold substrate is assumed with complex index of refraction 0.038-j*5.07 and an excitation wavelength of 700 nm. FIG. 3 shows the polarisation dependence of transmission of radiation on a logarithmic scale [dB] for a slit 1 with a width w of 200 nm, with a depth d of 1000 nm (curve 13) and 300 nm (curve 14) with TE polarised light and for a slit 1 with a width w of 200 nm and a depth d of 300 nm (curve 15), 600 nm (curve 16) and 1000 nm (curve 17) with TM polarised light. FIG. 4 shows the intensity (on a linear scale) along the centre line of a slit 1 (x=0) for TM polarised light and for a slit 1 with a depth of 300 nm (curve 18), 600 nm (curve 19) and 1000 nm (curve 20).

From FIG. 3 or FIG. 4 it can be concluded that:
1. Transmission for TM polarised excitation light through an aperture as defined above is significantly larger than for TE polarisation (see FIG. 3).
2. The intensity pattern for TM polarized light looks like a standing wave (interference pattern in the y-direction) (see FIG. 4).
3. A standing wave pattern (for TM polarization) is also present for higher depths (see FIG. 4, comparison of curves 18 to 20, which are all in case of TM polarized radiation, but for a different depth d of the slits 1. It can be seen that for increasing depths d (curves 18 through 20) that the excitation radiation, e.g. light, is still present at the output of the slit 1 (y=d), and does not attenuate considerably for positions y deeper into the slit 1.
4. There seems to be some kind of resonance effect (see FIG. 4, in particular curve 19) that depends on the depth d of the slit 1.

Thus, transmission of radiation through an aperture 1 shows a strong polarisation dependence, i.e. transmission for the TE polarisation state (E field parallel to the length L of the slit 1) is significantly lower than for TM polarisation state. The intensity distribution for TM polarised radiation inside the aperture 1 is a standing wave pattern which indicates a Fabry-Perot effect; this is also supported by the stronger maximum normalised intensity for a slit height of 600 nm (curve 19), i.e. the resonant effect. Behind the aperture 1, the intensity of TE polarised radiation rapidly drops which is attributed to divergence in the free space behind the slit 1.

In case of sub-diffraction limited pin-holes, as are used in prior art luminescence sensors as described above, a problem with the detection efficiency arises because the pin-holes also have sub-diffraction limited lateral dimensions for the luminescence, e.g. fluorescence, radiation. This means that just like the excitation radiation, the fluorescence radiation is also suppressed by the pin-holes, making it difficult for the fluorescence radiation to be detected, i.e. to reach a detector.

Because of the above, according to the invention, the excitation radiation 3, e.g. excitation light, is preferably polarised such that it is substantially suppressed by the apertures 1. However, since the generated luminescence radiation 5, 7, e.g. fluorescence radiation, is in most cases randomly polarised, on average at least 50% of the generated luminescence radiation 5, 7, e.g. fluorescence radiation, can leave the apertures 1 essentially without being suppressed. This is because the TE polarised part of the luminescence, e.g. fluorescence, radiation 5, 7 generated inside the aperture 1 is substantially suppressed by the aperture 1. The TM polarised part of the luminescence, e.g. fluorescence, radiation 5, 7 can escape from the apertures 1 both via the bottom and the top of the apertures 1. In order to avoid significant suppression of the luminescence, e.g. fluorescence, radiation 5, 7 by the apertures 1, the wavelength of the emitted radiation should be less than the minimum wavelength for which the second dimension of the apertures 1 is below the diffraction limit. This wavelength equals $2*L*n$, with n the diffraction limit of the medium that fills the apertures 1 and L the length of the apertures 1. This significantly increases the efficiency with which the generated luminescence radiation 5, 7, e.g. fluorescence radiation, is detected, compared to the known 'transmission mode'.

According to the invention, a detector 12 can be positioned at the same side of the substrate 11 where an excitation radiation source (not shown) is positioned, i.e. at the same side from which excitation radiation 3, e.g. excitation light, is sent toward the luminescence sensor 10. In the further description, the side of the substrate 11 at which the excitation radiation source and the detector 12 are positioned will be referred to as the front side 6 whereas the opposite side will be referred to as the back side 8 of the substrate 11.

In use, the luminescence sensor 10 according to the present invention may be immersed in an immersion medium, which may, for example, be a liquid or a gas such as water or air. The liquid or gas may comprise a substance, also called analyte molecules, for example, beads or molecules or labelled target molecules, to be sensed or detected by the luminescence sensor 10 according to the invention.

The luminescence sensor 10 as illustrated in FIG. 2 is illuminated from the front side 6 by excitation radiation, e.g. excitation light (indicated by arrow 3). According to the invention, the apertures 1 in the substrate 11 of the luminescence sensor 10 have a first lateral dimension, e.g. length L—which is not represented in FIG. 2, larger than the diffraction limit of the excitation radiation 3, e.g. excitation light, in the medium the apertures 1 are filled with, and a second lateral dimension, e.g. width w, with sub-diffraction limited sizes, i.e. a second lateral dimension is below the diffraction limit of the excitation radiation 3, e.g. excitation light, in the medium the apertures 1 are filled with.

The aperture 1 should have a second lateral dimension smaller than the diffraction limit of the excitation radiation 3, e.g. excitation light, in the immersion fluid i.e., should be smaller than half the wavelength inside the medium that fills the aperture 1, i.e. $<\lambda/(2*n)$; wherein n is the refractive index of the medium that fills the apertures 1 and $\lambda$ is the wavelength of the radiation source in vacuum.

As, according to the present invention, the detector 12 is positioned at the same side of the luminescence sensor 10 as the excitation radiation source (not shown), i.e. at the front side 6 of the wafer substrate 11 and thus at the front side of the luminescence sensor 10, luminescence radiation 5, e.g. fluorescence radiation, leaving the apertures 1 at the front side 6 of the wafer substrate 11 is detected by means of detector 12.

The detection of the intensity of the luminescence radiation 5, e.g. fluorescence radiation, may be done by any suitable detector 12, e.g. using charge coupled device (CCD) or complementary metal oxide semiconductor (CMOS) detectors. Alternatively, a scanning approach may be used in which only a small imaging view is obtained. Light is collected on a photodiode for a certain time in such a way that optimal signal to noise may be obtained. This may substantially increase the sensitivity of the sensor 10.

It has to be noted that, compared to sub-diffraction limited sensors working in transmission mode, the present invention has a drawback in that the apertures 1 do not aid in the suppression of the excitation radiation 3, e.g. excitation light, that is reflected by aperture(s) 1. For the sub-diffraction limited sensors 10 in 'transmission mode' this is the case because those sensors at least partially separate the excitation radiation 3, e.g. excitation light, and luminescence radiation 7, e.g. fluorescence radiation. Sensors 10 operated in 'reflection mode', however, do not suppress the reflected excitation radiation 4, e.g. excitation light, and thus the reflected excitation radiation 4, e.g. excitation light, also reaches the detector 12. As a consequence, the luminescence sensor 10 according to the present invention furthermore requires a wavelength filter 25 in front of the detector 12, i.e. in between the front side 6 of the sensor 10 and the detector 12. Examples of filters that can be used with the present invention are:

1) Notch filters that suppress a sufficiently narrow band around the wavelength of the excitation radiation 3, e.g. excitation light, effectively filtering out the excitation radiation 3, e.g. excitation light, almost completely, while the luminescence, e.g. fluorescence, radiation 5 is substantially not filtered because in most cases the wavelength where the luminescence radiation, e.g. fluorescence radiation 5 is maximum, is different from the wavelength of the excitation radiation 3, e.g. excitation light, and the wavelength bandwidth of the luminescence radiation 5, e.g. fluorescence radiation, is in general significantly larger than the bandwidth of the excitation radiation source.

2) As an alternative a band-pass filter can be used that transmits the luminescence, e.g. fluorescence, radiation 5 while substantially suppressing the excitation radiation 3, e.g. excitation light.

3) Based on similar arguments a high-pass filter may also be used in case the luminescence, e.g. fluorescence, radiation 5 occurs essentially for larger wavelengths than the wavelength of the excitation radiation 3, e.g. excitation light, or a low-pass filter can be used in case that the luminescence, e.g. fluorescence, radiation 5 occurs essentially for smaller wavelengths. The latter may be the case for e.g. second harmonic generation.

4) A specto-meter that spectrally resolves the combined reflected excitation radiation 3, e.g. excitation light, and the luminescence, e.g. fluorescence, radiation 5 can also be used.

The wavelength filter should show a strong suppression, preferably higher than two orders of magnitude, for the reflected excitation radiation 4, e.g. excitation light, but should show substantially no suppression for the luminescence radiation 5, e.g. fluorescence radiation, that radiates in the direction of the sensor 12. The transmission of luminescence, e.g. fluorescence radiation 5 through the wavelength filter, may preferably be better than 10% and more preferably may be better than 50%, still more preferred more than 70%. The aim of this filter is thus to block unwanted excitation radiation 4 that is reflected by the apertures 1 because the width w of the aperture 1 is smaller than the diffraction limit of the excitation radiation 3, e.g. excitation light, in the medium the apertures are filled with, while transmitting as much as possible the generated luminescence radiation 5.

An advantage of the luminescence sensor 10 according to embodiments of the present invention is that, because it comprises apertures 1 having a first lateral dimension larger than the diffraction limit of the excitation radiation in the medium the apertures 1 are filled with and a second lateral dimension below the diffraction limit of the excitation radiation in the medium that fills the apertures 1, and because it operates in 'reflection mode', the luminescence sensor 10 is able to efficiently measure concentrations of luminophores 2, e.g. fluorophores.

The reason why a luminescence sensor 10 used in 'reflection mode' has a better efficiency than a sensor used in 'transmission mode' can be understood as follows. The intensity of TE polarised excitation radiation 3, e.g. excitation light, experienced by the luminophores 2, e.g. fluorophores, decreases exponentially with increasing depth (away from the front side at which the excitation radiation source is positioned) of the luminophores 2, e.g. fluorophores, in the aperture 1.

For TM polarised luminescence, e.g. fluorescence, radiation this implies that, assuming the TM polarised luminescence, e.g. fluorescence, radiation is essentially not suppressed by the apertures 1, the 'in reflection' detected luminescence, e.g. fluorescence, radiation 5 decreases exponentially with increasing distance measured from the front side of the luminophore 2, e.g. fluorophore, in the aperture 1. For TM polarised luminescence, e.g. fluorescence, radiation there is no difference in the efficiency between transmission and reflection mode.

For TE polarised luminescence, e.g. fluorescence, radiation, the luminescent, e.g. fluorescent, signal is multiplied by an additional factor that decreases exponentially with increasing distance from the luminophore 2, e.g. fluorophore, inside the aperture 1 to the detector 12. A relatively simple mathematical analysis, where it is assumed that the decay constant α of the radiation inside the aperture 1 is similar for both the excitation radiation 4, e.g. light, and the luminescence, e.g. fluorescence, radiation 5, shows that combined efficiency scales with the distance y of the luminophore 2, e.g. fluorophore, in the aperture 1 according to:

$$\text{Exp}(-2*\alpha*y) \quad (1)$$

for detection in reflection mode, and $$\text{Exp}(-\alpha*d) \quad (2)$$

for detection in transmission mode, d being the depth of the aperture 1, which shows that the combined efficiency in reflection mode is better than in transmission mode for luminophores 2, e.g. fluorophores, at distances y<d/2. Moreover, the efficiency in transmission mode is independent of the distance y of the luminophore 2, e.g. fluorophore, and therefor the efficiency for y<d/2 is larger than for y>d/2. On average, where it is assumed that the position y of the luminophores 2, e.g. fluorophores, is normally distributed over the depth d of the aperture 1, the efficiency in reflection mode is better than in transmission mode, because the combined efficiency of such sensor not only depends on the position of the optically variable molecules inside the aperture 1.

On average, the luminescence sensor 10 used in reflection mode according to the present invention will have a larger efficiency compared to when the luminescence sensor 10 would be used in transmission mode.

In a preferred embodiment of the present invention, the luminescence sensor 10 comprises slits 1 as apertures. In that case, the first lateral dimension is the length (L) of the slit 1 and the second lateral dimension is the width w of the slit 1. In this case, the length of the slit 1 is larger than the diffraction limit of the excitation radiation 3, e.g. excitation light, in the medium the slit 1 is filled with. The width w of the slit 1 is lower than the diffraction limit of the excitation radiation 3, e.g. excitation light, in the medium the slit 1 is filled with, for example, lower than the diffraction limit of water when water is the fluid present in the slits 1. In particular cases, the first lateral dimension or length L may be larger than the diffraction limit of the excitation radiation 3, e.g. excitation light, in the medium the slit 1 is filled with, but may at the same time be lower than the wavelength of the excitation radiation 3, e.g. excitation light.

Figure 5:
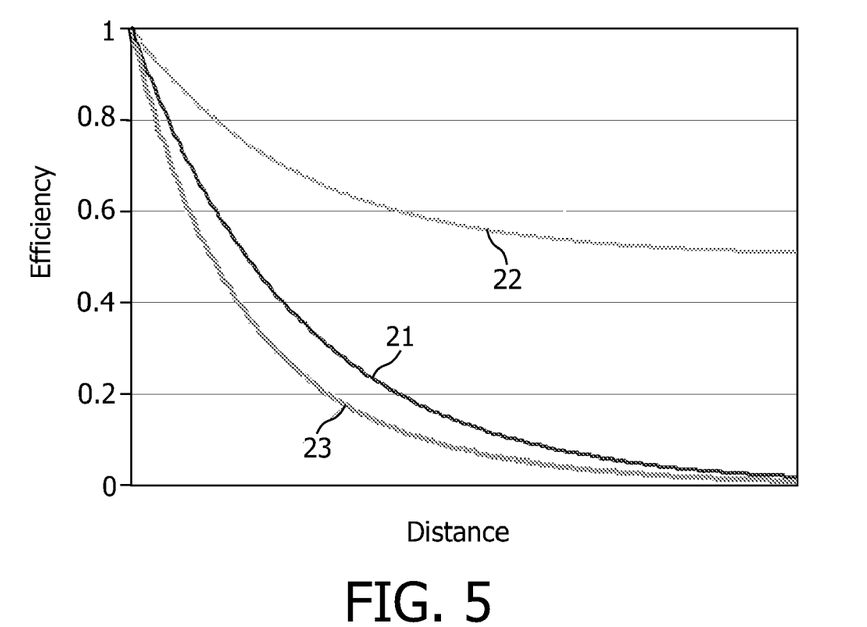
FIG. 5 illustrates the efficiency of excitation and luminescence detection for a slit biosensor operated in reflection mode.

FIG. 5 shows the excitation efficiency (curve 21), detection efficiency (curve 22) and combined efficiency (curve 23) for a luminophore 2, in the example given a fluorophore, as a function of the position within the slit 1 for a slit biosensor operated in reflection mode. The depth of the slit 1 is taken as twice the decay length of the field inside the slit 1. In this figure, it can be seen that the excitation efficiency (curve 21) is the highest at the entrance of the slit 1, because this is where the excitation radiation 3, e.g. excitation light, has the highest intensity. Since the biosensor is used in 'reflection mode', the luminescence radiation, e.g. fluorescence radiation, detection efficiency (curve 22) is also highest at this point. At the exit of the slit 1 both the excitation and detection efficiency (resp. curve 21 and 22) are the lowest. It has to be noted that, due to the polarization effect as described above, the detection efficiency (curve 22) at the lowest point is 50%, when it is assumed that on average the radiation generated by a luminophore 2, e.g. fluorophore, is 50% TE polarised and 50% TM polarised.

Figure 6:
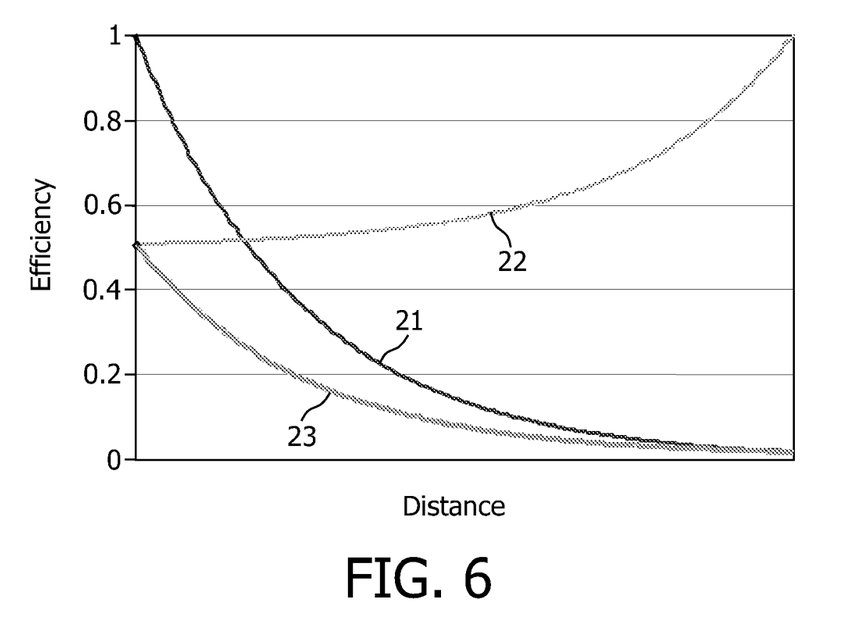
FIG. 6 illustrates the efficiency of excitation and luminescence detection for a slit biosensor operated in transmission mode.

For the sake of comparison, FIG. 6 shows the same curves, i.e. excitation efficiency (curve 21), detection efficiency (curve 22) and combined efficiency (curve 23), but now for a slit biosensor operated in 'transmission mode'. As expected, the detection efficiency (curve 22) is now highest at the exit of the slit 1.

By combining the effects of excitation and detection efficiency it is possible to compare the slits 1 in 'reflection mode' and in 'transmission mode'. It has been found by using equations (1) and (2) that the slits 1 in 'reflection mode' are giving 40% more luminescence signal, e.g. fluorescence signal, than in transmission mode, as it was assumed that the depth d of the slit 1 is twice the decay length of the filed in the slit 1.

Thus, the luminescence sensor 10 operating in 'reflection mode' according to the present invention has a larger luminescence signal, e.g. fluorescence signal, than the prior art sub-wavelength biosensors working in 'transmission mode'. Compared to the values obtained with the prior art 2D sub-wavelength biosensor in 'reflection mode' as described before, the gain in efficiency is about 47%.

In another embodiment according to the present invention, the apertures 1 may be ellipsoid apertures. In case of ellipsoid apertures, a first lateral dimension is slightly larger than the diffraction limit of the excitation radiation 3, e.g. excitation light, in the medium the ellipsoid apertures 1 are filled with and a second lateral dimension is slightly below the diffraction limit of the excitation radiation 3, e.g. excitation light, in the medium the ellipsoid apertures 1 are filled with. Preferably, the second lateral dimension is smaller than 80% of the diffraction limit of the excitation radiation (3) in said medium.

Compared to slits, these ellipsoid apertures 1 show a larger surface area, offering more binding sites for luminophores 2, e.g. fluorophores. Furthermore, when ellipsoid apertures 1 are created all through a wafer substrate 11, so that they can be used in a flow-through set-up, the wafer substrate 11 will be mechanically stronger than when slits are formed all through the wafer substrate 11. However, slits 1 show a better polarisation dependence than ellipsoid apertures 1 in the sense that due to the large length L, the suppression of TM polarised light will be significantly lower, provided that the length L of the ellipsoid apertures 1 is significantly smaller than the length L of the slits 1. This leads to a better detection efficiency. Therefor, the use of a sensor 10 having a substrate 11 comprising slits 1 is preferred above a sensor 10 having a substrate 11 comprising ellipsoid apertures 1.

In embodiments according to the present invention the selectivity of the luminescence sensor 10, for example luminescence biosensor or luminescence chemical sensor, may be improved by using surface immobilized ligands that can recognise one or more targets of interest, also called the analyte. In the case where more than one analyte has to be detected, the luminescence sensor 10 may comprise an array of different ligands. Examples of suitable ligands may be proteins, antibodies, aptamers, peptides, oligonucleotides, sugars, lectins, etc. The ligands may be immobilized to inner surface walls (indicated by reference number 24 in FIG. 2) of the at least one aperture 1 e.g. via suitable surface chemistry. The choice of surface chemistry depends merely on the chemical composition of the inner surface walls 24.

For example, when the apertures 1 are formed in a metal such as, for example, gold, silver, Cu or Al, self-assembled monomers can be deposited on the inner surface walls 24, for example using reactants that comprise a first reactive group, such as e.g. a sulfurhydryl group and/or a carboxylic group, which is suitable for binding to the inner surface walls 24 of an aperture 1. The reactant should furthermore comprise a secondary reactive group that can be used for immobilizing the ligand. For example, the secondary reactive group may be a carboxylic group that can be chemically activated to bind to primary amine groups of the ligand in aqueous solutions. Other immobilizing strategies to various different chemical surfaces are known in the art.

In embodiments of the invention the solution comprising the analyte can be pressed through the apertures 1 in order to facilitate binding of the analyte(s) to the ligand(s), e.g. by pumping. This pumping may be repeated several times. Alternatively a lateral flow can be used in which part of the fluid is going through the apertures 1.

It is to be understood that although preferred embodiments, specific constructions and configurations, as well as materials, have been discussed herein for devices according to the present invention, various changes or modifications in form and detail may be made without departing from the scope and spirit of this invention. For example, it has to be understood that the present invention is not limited to the use of slits or ellipsoid apertures as apertures 1 but that any other shape of apertures 1 having a first lateral dimension larger than the diffraction limit of the excitation radiation in the medium and a second lateral dimension below the diffraction limit of the excitation radiation in the medium, e.g. below the diffraction limit of the medium the apertures 1 are filled with, may be used.

The invention claimed is:

1. A luminescence sensor, comprising:
   a metal structure having at least one aperture, the at least one aperture being configured for being filled with a medium, wherein ligands are immobilized in the aperture;
   at least one optically variable molecule present in the at least one aperture,
   an excitation radiation source positioned at a first side of the metal structure for irradiating said at least one aperture with TE polarized excitation radiation for exciting said at least one optically variable molecule with an evanescent field created inside the aperture, wherein the excitation radiation is suppressed by the at least one aperture from reaching a second side of the metal structure that is opposite to the first side of the metal structure; and
   a detector positioned at the first side of the metal structure for detecting luminescence radiation generated by said at least one optically variable molecule excited by the evanescent field,
   wherein the at least one aperture has a first lateral dimension that is greater than the diffraction limit of the excitation radiation in the medium, and
   wherein the at least one aperture has a second lateral dimension less than the diffraction limit of the excitation radiation in the medium.

2. A luminescence sensor according to claim 1, wherein the second lateral dimension is smaller than 80% of the diffraction limit of the excitation radiation in said medium.

3. A luminescence sensor according to claim 1, the excitation radiation having a wavelength, wherein said first lateral dimension is less than the wavelength of the excitation radiation.

4. A luminescence sensor according to claim 1, wherein the first lateral dimension is larger than the wavelength of the radiation emitted from the optically variable molecules.

5. A luminescence sensor according to claim 1, the at least one aperture comprising inner surface walls, wherein ligands are immobilized on the inner surface walls of the at least one aperture.

6. A luminescence sensor according to claim 1, comprising an array of apertures.

7. A luminescence sensor according to claim 1, wherein the detector is a CCD or a CMOS detector.

8. A luminescence sensor according to claim 1, wherein the sensor is a luminescence biosensor.

9. A luminescence sensor according to claim 8, wherein the luminescence biosensor is a fluorescence biosensor.

10. The sensor of claim 1, wherein the medium is a liquid.

11. The sensor of claim 1, wherein the medium is water.

12. The luminescence sensor of claim 1, further comprising a transparent substrate on which the metal structure is disposed, wherein the transparent substrate is disposed between the excitation radiation source and the metal structure, and between the detector and the metal structure, such that the excitation radiation source provides the TE polarized excitation radiation through the transparent substrate to the metal structure, and the luminescence radiation generated by said at least one optically variable molecule is provided through the transparent substrate to the detector.

13. The luminescence sensor of claim 12, further comprising a wavelength filter disposed in between the transparent substrate and the detector, the wavelength filter being configured for suppressing reflected excitation radiation from reaching the detector.

14. The luminescence sensor of claim 1, further comprising a wavelength filter disposed in between the metal structure and the detector, the wavelength filter being configured for suppressing reflected excitation radiation from reaching the detector.

15. A method, comprising:
   providing at least one optically variable molecule in at least one aperture provided in a metal structure, the at least one aperture having a medium disposed therein wherein ligands are immobilized in the at least one aperture,
   exciting said at least one optically variable molecule by means of an evanescent field created in the aperture by illumination of the at least one aperture with a TE polarized excitation radiation emanating from an excitation radiation source positioned at a front side of said at least one aperture, wherein the TE excitation radiation is suppressed by the at least one aperture from reaching a back side of the at least one aperture that is opposite to the side,
   detecting luminescence radiation generated by said excited at least one optically variable molecule by a luminescence detector disposed on a same front side of the structure as the excitation radiation source,
   wherein the at least one aperture has a first lateral dimension, that is larger than the diffraction limit of the excitation radiation in said medium, and
   wherein the at least one aperture has a second lateral dimension smaller than the diffraction limit of the excitation radiation in said medium.

16. A method according to claim 15, wherein the second lateral dimension is smaller than 80% of the diffraction limit of the excitation radiation in said medium.

17. A method according to claim 15, the excitation radiation having a wavelength, wherein said first lateral dimension is less than the wavelength of the excitation radiation.

18. A method according to claim 15, the at least one aperture comprising inner surface walls, wherein the method furthermore comprises immobilizing the ligands to the inner surface walls of the at least one aperture.

19. The method of claim 15, wherein the medium is water.

20. The method of claim 15, further comprising suppressing reflected excitation radiation from reaching the luminescence detector by a wavelength filter disposed between the metal structure and the luminescence detector.

* * * * *